United States Patent [19]

Kigasawa et al.

[11] Patent Number: 4,695,465

[45] Date of Patent: Sep. 22, 1987

[54] SOFT PATCH

[75] Inventors: Kazuo Kigasawa; Hideaki Ohtani; Makoto Tanaka; Shigeru Hayashida, all of Tokyo, Japan

[73] Assignee: Takeda Chemical Industry, Ltd., Osaka, Japan

[21] Appl. No.: 720,401

[22] Filed: Apr. 5, 1985

[30] Foreign Application Priority Data

Apr. 5, 1984 [JP] Japan ................................. 59-66710
Feb. 13, 1985 [JP] Japan ................................. 60-24393

[51] Int. Cl.⁴ ...................... A61L 15/03; A61F 13/00
[52] U.S. Cl. ..................................... 424/449; 424/445; 424/447; 424/448; 514/774; 514/946; 514/947; 604/896; 604/897
[58] Field of Search .......................... 424/19, 22, 28; 604/896, 897; 514/773, 774, 775, 946, 947

[56] References Cited

U.S. PATENT DOCUMENTS 3,249,109 9/1981 Maeth et al. .................. 128/268
4,298,749 9/1981 Keith et al. ..................... 424/28
4,572,832 2/1986 Kigasawa et al. ............... 424/19

Primary Examiner—Shep K. Rose
Attorney, Agent, or Firm—Antonelli, Terry & Wands

[57] ABSTRACT

Drug preparations for external application having a stick-itself-to-the-skin property, so-called "soft patch", are provided. The preparations contain a drug, a water-soluble protein having an absorption-promoting effect, a polyhydric alcohol a tackifier, and an oleaginous substance, and ensure an improved percutaneous absorption and bioavailability of the drugs, thus permitting an accurate control of drug dosage.

15 Claims, No Drawings

SOFT PATCH

This invention relates to pharmaceutical preparations for external application.

As examples of pharmaceutical products for application to the skin, ointments, liquids, plasters, tapes, etc. are known. These preparations are, however, not fully satisfactory in regard to dosage establishment, release and penetrability of active component, bioavailability, feeling of use, etc. Taking ointments as an example, it is difficult to apply an accurate dose, which depends on the application area and thickness; and it has also been pointed out that these preparations cannot be expected to produce adequate systemic effects after percutaneous absorption. Moreover, in the case of external drugs as compared with oral and other products, the skin acts as a barrier to the absorption of the drug and their bioavailability is considerably low. Of late, new dosage forms generally called the drug delivery system are being developed, but they have been put to use only with a few specific drugs. Japanese Kokai Sho No. 56-71025 discloses hydrophilic and good water-holdable base for plaster containing gelatin, polyvinylalcohol or polyvinylpyrrolidone, sodium polyacrylate, carboxyvinyl polymer, polyhydric alcohol such as glycerin and water, in addition to, for example, methyl salicylate. But this process is not satisfactory yet.

In view of the above technical situation, the present inventors conducted an intensive research to develop pharmaceutical preparations for external use that would overcome the above-mentioned disadvantages and, as a result, found that external preparations containing a water-soluble protein display an improved percutaneous absorption. The finding was followed by further studies which have resulted in the development of external preparations of this invention which ensure an improved bioavailability, permit an accurate control of drug dosage and are convenient to apply.

For the purpose of accomplishing the above objects, defined components inclusive of said watersoluble protein are incorporated in the preparations according to this invention. Thus, this invention relates to a soft pharmaceutical preparation for external application which contains the following components (a), (b), (c), (d), and (e) and has a stick-itself-to-the-skin property (the preparation will sometimes be referred to briefly as "soft patch").

(a) a drug;
(b) a water-soluble protein which has an absorption-promoting effect;
(c) a polyhydric alcohol;
(d) a tackifier; and
(e) an oleaginous substance.

There is no limitation on the type of drug that can be used, provided that it can be absorbed percutaneously. Thus, the above-mentioned drug includes both the drugs topically applied for local effects and those administered for systemic effects. The topical drugs include the drugs administered for the purpose of curing diseases on the skin surface or under the skin or for protective conditioning of the skin, and display mainly local effects. The drugs for systemic administration are the drugs absorbed from the skin surface where they are applied and reach the target tissue or organ via the circulation to display mainly systemic effects. Such drugs include antimicrobial agents, antitumor drugs, vitamins, antidiabetics, enzymes, herb medicines, crude extracts and other medicines which take effect in the circulatory system, nervous system, endocrine system, respiratory system, metabolic system, urinary organ system, and digestive organ systems, of which practical examples are partially listed below.

(1) Analgesic antiinflammatory agents: acetaminophen, aspirin, salicylic acid, methyl salicylate, choline salicylate, glycol salicylate, l-menthol, camphor, mefenamic acid, fluphenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexamac, piroxicam, phenylbutazone, oxyphenbutazone, clofezone, pentazocine, mepirizole, etc.: (2) steroid antiinflammatory agents: hydrocortizone, prednisolone, dexamethasone, triamcinolone acetonide, fluocinolone acetonide, fludrocortisone acetate, etc.; (3) antihistaminics or antiallergic agents: chlorpheniramine, glycyrrhizic acid, diphenhydramine, periactin, etc.; (4) local anesthetics: benzocaine, procaine, dibucaine, lidocaine, etc.; (5) antimicrobial agents including antibacterial agents, antifungal agents, antimycotic agents and antiviral agents; tetracyclines such as oxytetracycline, penicillins such as ampicillin, cephalosporins such as cefalotin, aminoglycosides such as kanamycin, macrolides such as erythromycin, chloramphenicol, iodides, nitrofrantoin, nystatin, amphotericin, fradiomycin, sulfonamides, purrolnitrin, clotrimazol, etc.; (6) antihypertensive agents: clonidine, α-methyldopa, reserpine, syrosingopine, rescinnamine, cinnarizine, hydrazine, prazosin, etc.; (7) antihypertensive diuretics: theophylline, trichlormethiazide, furosemide, tripamide, methylclothiazide, penfluzide, hydrothiazide, spironolactone, metolazone, etc.; (8) cardiotonics: digitalis, ubidecarenone, dopamine, etc.; (9) coronary vasodilators: nitroglycerin, isosorbitol dinitrate, erythritol tetranitrate, pentaerythritol tetranitrate, dipyridamole, dilazep, trapidil, trimetazidine, etc.; (10) vasoconstrictors: dihydroergotamine, dihydroergotoxine, etc.; (11) β-blockers or antiarrythmic agents: pindolol, propranolol, etc.; (12) calcium antagonists and other circulatory organ agents: diltiazem, nifedipine, nicardipine, verapamil, bencyclane, ifenprodil tartarate, molsidomine, etc.; (13) anti-convulsants: nitrazepam, meprobamate, phenytoin, etc.; (14) agents for dizziness: isoprenaline, betahistine, scopolamine, etc.; (15) minor tranquilizers: diazepam, lorazepam, flunitrazepam, fluphenazine, etc.; (16) hypnotics and sedatives: phenobarbital, amobarbital, cyclobarbital, etc.; (17) muscle relaxants: tolperisone, baclofen, dantrolene sodium, cyclobenzaprine; (18) autonomic agents: atropine, levodopa, etc.; (19) respiratory agents: codeine, ephedrine, isoproterenol, dextromethorphan, orciprenaline, ipratropium bromide, cromglycic acid, etc.; (20) hormones or antihormones: corticotropin, oxytocin, vasopressin, testosterone, progesterone, estradiol, salivary hormone, thyroid hormone, adrenal hormone, kallikrein, insulin, oxendolone, etc.; (21) vitamins: vitamins A, B, C, D, E and K and derivatives thereof, calciferols, mecobalamin, etc.; (22) antitumor agents: 5-fluorouracil and derivatives thereof, krestin, picibanil, ancitabine, cytarabine, etc.; (23) enzymes: lysozyme, urokinaze, etc.; (24) herb medicines or crude extracts: glycyrrhiza, aloe, Sikon (Lithospermi Radix), etc.; (25) antiulcer agents: allantoin, aldioxa, alcloxa, N-methylscopolamine methylsulfate, etc.; (26) antidiabetics; etc.

The drugs mentioned above can be used in combination as required. Moreover, the above drugs may be used either in the free form or, if capable of forming salts, in the form of a salt with a suitable acid or base. If the drugs have a carboxyl group, their esters can be employed.

The acid mentioned above may be an organic acid, for example, methanesulfonic acid, lactic acid, tartaric acid, fumaric acid, maleic acid, acetic acid, or an inorganic acid, for example, hydrochloric acid, hydrobromic acid, phosphoric acid or sulfuric acid. The base may be an organic base, for example, ammonia, triethylamine, or an inorganic base, for example, sodium hydroxide or potassium hydroxide. The esters mentioned above may be alkyl esters, aryl esters, aralkyl esters, etc.

Among them, the drugs acting in the circulatory system, nervous system, endocrine system and respiratory system, antimicrobial agents and enzymes are particularly used as preferable drugs for this invention.

Although this invention may be applied to all types of drugs as listed hereabove, among such drugs, the drugs which, when administered alone, are not or only sparingly absorbed percutaneously, the drugs which, if administered orally, show only low rates of utilization in the body, for example, drugs with bioavailabilities of less than 80%, drugs which tend to produce many side effects, drugs which are decomposed by digestive juice, etc. and have, therefore, to be administered by injection, and drugs which are subject to the first-pass effect in the liver, etc. are especially effective when this invention is applied.

The concentration of the drug need only be that which exhibits the expected clinical effect, and in many instances ranges from about 0.01 to 15 weight percent, preferably 0.05 to 10 weight percent, or more preferably 0.05 to 5 weight percent, based on the weight of the whole composition. The dosage is adjusted according to the type of drug, object of medication, age and body weight of the patient, stage of disease, etc.

The water-soluble protein mentioned hereinbefore may be virtually any such protein that promotes absorption of the drug used. Such a protein may be a naturally occurring protein or a non-natural protein. The former includes animal proteins and vegetable proteins, while the latter includes peptides artificially derived or synthesized. While there are fields of technology where a sharp distinction is made between peptide and protein, peptides are included in the category of proteins for the purposes of this invention, this being in consideration of their action and effect.

Examples of said animal proteins include gelatin, solubilizable collagen, casein and its sodium salt, glue, and their hydrolysates. The gelatin and solubilizable collagen include the soluble proteins obtainable by acid or alkali hydrolysis or hot water treatment of proteins from animal bones or skins and the products derived therefrom by suitable chemical modifications, for example, succinylation, maleylation, phthalation, and they range from about tens of thousand to hundred of thousand in molecular weight. Typical of said vegetable proteins are soybean protein, for example, the protein obtainable by sedimentation and enzymatic treatment of the water-soluble fraction of solvent-extracted soybean cake, and soybean casein. The peptides mentioned above include the peptides obtainable by homo- or hetero-condensation of amino acids by such techniques as chemical synthesis, fermentation or semi-synthesis, and their molecular weights are generally in the range of a few hundred to tens of thousand. As such, the constituent amino acids of the peptides may be neutral, basic or/and acidic, optically active or/and racemic, natural or/and synthetic. In accordance with this invention, one ore more, preferably one or two, of such water-soluble proteins can be employed. For instance, gelatin can be used either alone or in admixture with casein or soybean protein. Moreover, in consideration of promotant effects on drug absorption, compatibility or dispersability with other components, ease of availability, etc., gelatin, solubilizable collagen, casein, soybean protein, etc. are generally utilized with advantage.

The amount of said water-soluble protein need only be that which helps accomplish the objects of this invention, and preferably that which ensures a sufficient promoting effect on the percutaneous absorption of the drug used. For this purpose, the water-soluble protein is in many instances used in an amount substantially equal to or surpassing the amount of the drug, generally in a proportion of about 5 to 50 weight percent, preferably about 5 to 35 weight percent, more preferably 10 to 30 weight percent, based on the whole composition.

The above-mentioned polyhydric alcohols may include those having 2 to 6 alcoholic hydroxyl groups. Such polyhydric alcohols include glycols, triols and polyols having 4 to 6 alcoholic hydroxyl groups. Typical of said glycols are glycols containing 2 to 6 carbon atoms, e.g. ethylene glycol, propylene glycol, butylene glycol, polyethylene glycol (average molecular weight about 200-8,000, preferably about 200 to 6,000), etc. Examples of said triols include glycerin, trimethylolpropane, etc. Said polyols are exemplified by sorbitol (sorbit), polyvinylpyrrolidone, etc. These polyhydric alcohols may be used either singly or in combination (preferably, of two or three). Thus, for example, glycerin alone or a mixture of glycerin and butylene glycol is employed.

Among those polyhydric alcohols, those which satisfy the requirements such as the adjustment and maintenance of softness of the external drug of the invention, compatibility or co-dispersibility with the other components, and sufficient wettability of the product at application, may be freely used, and especially those which are low in volatility and plastic, are generally preferred and, in this sense, glycerin, propylene glycol, butylene glycol, sorbitol, etc. may be commonly employed.

The proportion of said polyhydric alcohols depends on the purpose of incorporation, types of other components, etc. and cannot be stated in general terms but may generally range from about 5 to 50 weight percent, preferably from about 5 to 35 weight percent, more preferably 10 to 30 weight percent, based on the whole composition.

As to the tackifier referred to hereinbefore, a substance or substances capable of providing the preparation with adequate adhesivity to the skin may be used. Preferred tackifiers are those which not only bestow adhesivity to the skin but serve the purpose of assisting in the maintenance of flexibility of the product itself and that of preventing evaporation of water and others through formation of a surface film. Thus, cellulose derivatives, polysaccharides, carboxyvinyl polymers, polyvinyl alcohol, polyvinylpyrrolidone, etc. may be mentioned as typical tackifiers.

The above-mentioned cellulose derivatives include alkylcelluloses and hydroxyalkylcellulose whose average molecular weights are in the range of about 40,000 to 200,000 and whose alkyl moieties contain 1 to 4 carbon atoms, e.g. methylcellulose, ethylcellulose, propylcellulose, methylpropylcellulose, hydroxymethylcellulose, hydroxyethylcellulose, hydroxypropylcellulose, and carboxymethylcellulose and its alkali metal salts, etc.

Examples of said polysaccharides include simple polysaccharides such as starch and its derivatives, e.g. carboxymethylstarch, hydroxypropylstarch, dextrin, dextran, chitin, alginic acid and its sodium salt, glycogen, Pluran ® (the trademark of Hayashibara in Japan), carrageenan, etc., and complex polysaccharides such as mannan, peptin, gum arabic, Karaya gum, etc.

The above-mentioned carboxyvinyl polymers are those having average molecular weights in the range of about 900,000 to 3,000,000, and include polyacrylic acid, polymethacrylic acid and their alkali metal salts. To be specific, such commercial products as Hiviswako ® (the trademark of Wako Pure Chemical Industries, Ltd. in Japan), Carbopol ® (the trademark of Goodrich in U.S.A.), Luviskol ® (the trademark of BASF in West Germany), etc. can be advantageously employed. The tackifiers mentioned above are used either singly or in combination (preferably, of two or three).

In using such a tackifier in the practice of invention, its proportion should be such that the above-mentioned objects are fulfilled and, thus, generally ranges from about 0.1 to 15 weight percent and preferably from about 0.3 to 10 weight percent, more preferably 0.5 to 10 weight percent, relative to the whole preparation.

As the oleaginous substance referred to hereinbefore, fatty acid esters, aliphatic higher alcohol, paraffin oil, lanolin oil, silicone oil, Plastibase ® (the trademark of Squibb and Sons, U.S.A.) may be used.

Said fatty acid esters are esters of aliphatic carboxylic acid with aliphatic alcohol, which may be either synthetic products or natural products. The range of this aliphatic carboxylic acid includes saturated or unsaturated aliphatic mono- or di-carboxylic acid, of which representative example includes lower to higher fatty acid having 2 to 24 carbon atoms, and among them middle to higher fatty acid containing 6 to 20 carbon atoms are often used as preferable ones. Their practical examples include acetic acid, propionic acid, hexanoic acid, capric acid, caprylic acid, octanoic acid, dioctanoic acid, adipic acid, sebacic acid, palmitic acid, stearic acid, oleic acid, linolic acid, linolenic acid, and myristic acid.

Examples of said aliphatic alcohol are saturated or unsaturated aliphatic monools or triols having 1 to 30, preferably 1 to 20 carbon atoms and polyols having 4 to 8 hydroxyl groups. Examples of said monools include straight-chain or branch alcohols, for example, methanol, ethanol, propanol, butanol, hexanol, octanol, decanol, hexadecanol, octyldodecylalcohol, palmitylalcohol, stearylalcohol, and myristylalcohol. An example of triols is glycerin, and said polyols may be represented by sorbitol (sorbit) and cane sugar. As the esters of said aliphatic carboxylic acid and aliphatic alcohol, those of which carboxylic groups and alcoholic hydroxylic groups in the molecule are wholly engaged in the esterification (complete esters) are preferable, or as the case may be, those in which one of carboxylic groups in the aliphatic dicaroxylic acid molecule or/and part of hydroxyl group in tri- or poly-ol molecule is freed (partial esters) may be used, or esters of mixed acid group may be also used.

Above all, middle to higher fatty acid glyceride or triglyceride having 6 to 20 carbon atoms, complete esters of middle to higher fatty acid having 6 to 20 carbon atoms and aliphatic monool having 1 to 20 carbon atoms, or partial esters with polyol may be preferably used. Examples of said fatty acid esters are isopropyl myristate, octyldodecyl myristate, myristyl myristate, isoprypyl palmitate, butyl stearate, decyl oleate, diisopropyl adipate, diethyl sebacate, hexyldecyl dioctanate, sorbitan monopalmitate, cane sugar fatty acid ester, triacetyn, di- or tri-glyceride caprylate, di- or tri-glyceride caprate, mixed acid group triglyceride comprising capric acid and caprylic acid, di- or triglyceride oleate, di- or tri-glyceride linolate, and mixed acid group triglyceride comprising oleic acid and linolic acid.

Such fatty acid esters may be used either in a pure or nearly pure state as in synthetic products, or in a mixed state with other substances as in natural products. Former examples are the substances exemplified hereabove being used directly, whereas latter examples may include natural oils and fats, such lard, tallow, whale wax and other animal oils, or soybean oil, sesame oil, cotton seed oil, palm oil, olive oil, castor oil, beewax and other vegetable oils.

Examples of said aliphatic higher-alcohols are represented by saturated or unsaturated aliphatic alcohols having 14 to 20 carbon atoms, such as cetanol (palmityl alcohol), stearyl alcohol, oleyl alcohol, and hexadecyl alcohol.

Examples of said paraffin oils are mainly composed of paraffin mixtures having 15 or more carbon atoms, and practically are liquid paraffin, vaseline including white vaseline, squalane, and squalene, and particularly liquid paraffin, white vaseline and squalane are often used preferably.

Examples of said silicone oils are polymer mixtures of dimethyl siloxane, e.g. dimethyl polysiloxane, and its alkyl ester, methyl phenyl polysiloxane, glycolmethyl siloxane, etc.

Examples of said lanolin oils are lanolin, lanolin wax, hydrogenated or reduced lanolin and its ethylene oxide polymer, and among them lanolin is often used most preferably.

The chemical composition of this lanolin is usually as follows: alcohols, e.g. cetyl alcohol, lanolin alcohol, carnaubyl alcohol, by 30 to 35 weight percent, cholesterins, e.g. cholesterin, isocholesterin, methacholesterin, by 15 to 20 weight percent, fatty acids, e.g. acetic acid, lactic acid, caproic acid, myristic acid, stearic acid, lanostearic acid, by 45 to 55 weight percent, etc.

Among these oleaginous substances, those having an action to promote the percutaneous absorption of the drug and an action to enhance the solubility of the drug and nonirritant to the skin are particularly used preferably. Such oleaginous substances exist mostly in a liquid or paste state, or sometimes in a wax state, and may be used regardless of the state, and usually commercial products may be used advantageously.

In this invention, the above-mentioned oleaginous substances may be used either singly or in combination (preferably, of two to four).

The proportion of said oleaginous substances depends on the purpose of the invention, and usually ranges from 0.1 to 25 weight percent, preferably 0.5 to 20 weight percent, or more preferably 0.5 to 15 weight percent, based on the whole composition.

In addition to the above components, for the purpose of maintaining the product characteristics such as softness and drug absorption of the soft patch, an appropriate amount of water may be added. The proportion of water is generally about 20 to 80 weight percent, preferably 30 to 75 weight percent, or more preferably 35 to 70 weight percent, based on the whole preparation.

In addition of above components, for the purpose of permitting the desired characteristics of the soft patch to be fully materialized, other additives may also be used as necessary. Such additives may be known substances, examples of which are as follows.

(1) Absorption promoting auxiliaries (substances that contribute to the absorption of drugs through promotion of softening of the horny layer, improvement of water retention or absorption, dilatation of pores of the skin, etc.): Urea, salocolumn, 1-n-dodecylazocycloheptan-2-one (trademark: Azon ®, Nelson Research Development Co. in U.S.A.), dimethyl sulfoxide, dodecyl sulfoxide, dimethylformamide, dimethylacetamide, toluyl diethylamide, tetrahydrofurfuryl alcohol, dodecylpyrrolidone, 2-pyrrolidone, methylpyrrolidone, allantoin, salicylic acid, etc. When such an absorption-promoting auxiliary agent as above is employed, its proportion is generally about 0.05 to 5 weight percent, preferably 0.1 to 5 weight percent, based on the whole preparation.

(2) Preservatives (substances which prevent degradation or putrefaction due to microorganisms): p-Hydroxybenzoic acid alkyl esters (parabens), sorbic acid, dehydroacetic acid, etc. When such a preservative is employed, its proportion is generally about 0.05 to 2 weight percent, preferably 0.1 to 1 weight percent, relative to the whole preparation.

(3) Emulsified-dispersants (substances that contribute to a uniform dispersion of the components, etc.): Non-ionic surfactants such as polyoxyethylene fatty acid esters, Polysorbate 80, etc., anionic surfactants such as sodium laurylsulfate, etc., lower alcohols such as ethanol, etc., acetone and so on. When such an emulsifier-dispersant is employed, its final concentration is generally about 0.05 to 5.0 weight percent, preferably 0.1 to 3 weight percent, relative to the whole preparation.

(4) pH-controlling agents (substances possessing abilities to stabilize the components, lessen the irritation to the skin, and maintain the absorption of drug through controlling of pH): Organic acids, e.g. citric acid, tartaric acid, lactic acid, or inorganic acids, e.g. hydrochloric acid, sulfuric acid, phosphoric acid, or their alkaline metal salts. When such a pH-controlling agent is used, its proportion is generally about 0.1 to 5 weight percent, preferably 0.5 to 5 weight percent, relative to the whole preparation.

(5) Colors: Water-soluble tar colors, natural colors, etc.

In the practice of this invention, unlike in the production of the conventional gelatin cataplasm, it is not necessary to use a crosslinking agent, e.g. aldehydes, or a stringent, e.g. zinc oxide, kaolin. Rather, such additives may detract from the softness of the preparation.

The dimensions of the unit dosage form of the soft patch composed of the above components are optional only if the soft patch has a size and shape permitting easy application to the skin surface. Thus, generally, it may be shaped like a sheet, a disk, a ribbon or the like, which has a suitable thickness and area (the effective area to come in contact with the skin surface when applied). The above-mentioned thickness is generally about 0.2 to 3 mm and preferably about 0.3 to 2.0 mm. The area is generally about 0.08 to 200 cm$^2$ and preferably about 0.2 to 160 cm$^2$. Thus, taking a sheet-shaped soft patch as an example, its area may generally be about 0.2 by 0.4 cm to 10 by 20 cm and preferably be about 0.4 by 0.5 cm to 10 by 16 cm. In the case of disk or ribbon-shaped soft patches, too, various sizes may be selected from within the above-mentioned range. Which of these shapes to choose depends upon the administration site, therapeutic purpose, etc.

The soft patch having any of the above-mentioned shapes is generally made available in independent single-dose units but for convenience in use, it may be made available as a sheet provided with incisions or scores for severing it into single-dose units, as an integral sheet from which several to tens of dose units can be serially cut off with scissors or the like, or as a roll of the ribbon-shaped soft patch.

When the soft patch is covered with a suitable packaging film on one side or both sides thereof for the ease of use, storage or handling, the film is removed in use and the exposed medicated side is applied to the skin. Such a packaged product is convenient in many cases. Therefore, the soft patch can be made available in the various alternative forms described below. (1) No packaging film is used at all. (2) A packaging film is used on one side only. (3) A packaging film is used on both sides. As the packaging film, a flexible film having a thickness of about 0.02 to 0.8 mm, such as synthetic resin films, e.g. polyethylene film, polypropylene film, elastomer film, butadiene polymer film, isoprene polymer film, etc., cellophane film, etc. can be employed. A woven or nonwoven fabric may also be employed.

When the soft patch contains a volatile component or there is a risk of contamination during storage, it is preferably stored in a sealed container, e.g. aluminum pack, polyethylene pouch, moisture-proof paper bag, etc.

The external preparation according to this invention is generally soft in texture. As will be seen from the fact that it has a softness allowing some degree of deformation without losing its integrity, the external preparation of this invention has adequate flexibility and elasticity so that, for example, it can be easily stretched or dented by application of minor external forces. Therefore, it fits the skin well and provides a good feeling of use. It should be understood that the concept of softness in the context of this invention covers the case in which the softness of the soft patch increases when its surface is wetted with water, for instance.

The soft patch having the above-described construction is applied for therapeutic purposes to the skin of the body at the site suitable for the therapeutic purpose, subject, etc. For example, for topical administration, the soft patch is applied directly to the affected site or in the neighborhood thereof. For systemic application, it is applied to a site which is most conductive to the percutaneous absorption of the active component, e.g. where the horny layer has not been well developed, or a site which does not give a substantial foreign sensation to the patient. Furthermore, the known cosmetic ingredients may be incorporated for use as a cosmetic product (prevention of rough skin, sun-burn, etc.).

As regards the production of the soft patch, a variety of processes may be utilized unless they are in conflict with the purposes of this invention. For example, the existing processes for the production of pharmaceutical products such as suppositories, cakes and confections such as chewing gum, jellies, chocolate, etc. or foods such as noodles may be modified in part to utilize them as the production processes for the soft patch of this invention. Such modifications are those necessary for the maintenance of softness, improvement of drug absorption, etc. which are the objects of this invention. A convenient production method is as follows. The above-mentioned drug, water-soluble protein, polyhydric alcohol, tackifier and oleaginous substance are mixed in a suitable sequence and the mixture is molded into a product having a suitable shape. To be specific, (a), (1) a mixture of water-soluble protein and water, (2) a mixture of drug, polyhydric alcohol, oleaginous substance and water (to which the above-mentioned additives are added at this stage), and (3) a mixture of tackifier and water are respectively prepared. Then, (4) the above mixtures are blended generally in the order mentioned and stirred until a homogenous mixture is obtained. Finally, (5) in the molding stage, it may generally be cast in a vessel having suitable thickness and dimensions or compression-molded using a suitable mold and the molding is then cut, punched or otherwise processed into the unit dosage form. In an alternative process, (b), a liquid other than water, e.g. a polyhydric alcohol may be used in lieu of water. In still another alternative process, (c), the components are comminuted or kneaded irrespective of the presence of water, and the mixture is compression-molded using a suitable mold. In the course of the above process or thereafter, the above-mentioned packaging film may be applied. Since the above method consists of simple and expedient steps, it can be advantageously practiced on a commercial scale and permits production of the soft patch in a variety of shapes and forms suitable for varied uses. Moreover, even drugs which are either liquid or low-melting and could not be incorporated in the conventional solid preparations can now be incorporated by the process described above.

The following examples illustrate the method of producing the external preparation of this invention. The formulas of the products described in the examples are shown in Table 1.

EXAMPLE 1

Clidanac-containing preparation; pharmaceutical compositions will herein after be referred to in the like manner.

According to the formula given in Table 1, (1) 15 g of gelatin was put in 30 g of purified water and dissolved by warming at 50° C.;

(2) 1 g of Pluran ® and 1 g of polyvinyl alcohol were dissolved in 17.7 g of purified water;

(3) 0.5 g of sodium polyacrylate was dissolved in 10 g of purified water;

(4) in a mixture of 23 g of glycerin, 0.5 g of diisopropyl adipinate and 0.2 g of Polysorbate 80 were suspended 1 g of clidanac and 0.1 g of paraben with warming at 50° C.;

(5) the solution (2) was added to the solution (1) and the mixture was stirred at the same temperature as above using a homomixer;

(6) the solution (3) was added to the above mixture (5) and the whole mixture was stirred in the homomixer at the same temperature; and (7) the suspension (4) was added to the above mixture (6) and the whole mixture was stirred in the homomixer at the same temperature and, then, cast into a mold in a thickness of 1 mm over a polyethylene packaging film, and was cut to give a soft patch in the shape of a sheet measuring 6 cm (length) by 4 cm (width).

EXAMPLE 2

Pindolol-containing preparation.

The bulk product prepared by the same procedure as Example 1 in accordance with the formula of Table 1 was shaped into a ribbon measuring 1 mm in thickness and 2.0 cm in width. After application of a packaging film, the ribbon was rolled up in the shape of a coil.

EXAMPLE 3

Clidanac-containing preparation.

The bulk product prepared in the same procedure as Example 1 in accordance with the formula of Table 1 was cut into a sheet-shaped product measuring 1 mm in thickness by 13 cm in length by 10 cm in width.

EXAMPLE 4

Ifenprodil tartrate-containing preparation.

According to the formula given in Table 1, (1) 2 g of sodium citrate was dissolved in 32.3 g of purified water, and 20 g of gelatin and 2 g of Pluran were added to wet, and dissolved by warming at 50° C.;

(2) 0.5 g of sodium polyacrylate was dissolved in 5 g of purified water;

(3) 1 g of Polysorbate 80 was dissolved in 5 g of purified water;

(4) 1 g of ifenprodil tartrate and 0.2 g of paraben were added to 23 g of glycerin, and dissolved by warming at 70° C.;

(5) 5 g of middle-chain fatty acid triglyceride and 3 g of white vaseline were uniformly mixed by warming at 50° C; and (6) in a homomixer heated to 50° C., solutions (2) and (3) were first added to mixture (1), and solution (4) was added, then finally solution (5) was added, and the whole mixture was stirred and cast into a mold. After cooling, the casting was cut to give a soft patch containing 20 mg of ifenprodil tartrate in a thin film measuring 6.5 cm in length by 6.5 cm in width by 0.4 mm in thickness.

EXAMPLES 5–22

Ifenprodil tartrate-containing preparations.

According to the formula of Table 1, soft patches were prepared in the same manner as Example 4. The obtained bulk products were manufactured into a disk-shaped film soft patch measuring 0.4 mm in thickness by 30 mm in diameter by blanking or cutting in Example 7, into a tape-formed soft patch with polyethylene packaging film measuring 0.4 mm in thickness by 2.5 cm in width being rolled up in a coil in Example 9, and into a soft patch similar to the form in Example 4 in all other examples.

EXAMPLES 23–

Clonidine hydrochloride-containing perparations.

The bulk products obtained by the same procedure as Example 4 in accordance with the formula of Table 1 were cut to manufacture thin film soft patches containing 0.3 mg of clonidine hydrochloride measuring 2 cm in length by 2 cm in width by 0.4 mm in thickness.

EXAMPLES 28–32

Nifedipine-containing preparations.

According to the formula of Table 1, soft patches were prepared in the same manner as Example 4.

EXAMPLES 33–35

Prazocin hydrochloride-containing preparations.

The bulk products obtained by the same procedure as Example 4 in accordance with the formula of Table 1 were cut to manufacture thin film soft patches containing prazosin hydrochloride by 1 mg measuring 2 cm in length by 2 cm in width by 0.4 mm in thickness.

EXAMPLES 36–40

Clidanac-containing preparations.

In Example 36, according to the formula given in Table 1, (1) 20 g of gelatin and 2 g of Pluran were wetted in 41.3 g of purified water, and dissolved by warming at 50° C.;

(2) 0.2 g of paraben was dissolved in 23 g of glycerin by warming at 50° C.;

(3) 0.5 g of sodium polyacrylate was dissolved in 5 g of purified water;

(4) 1 g of Polysorbate 80 was dissolved in 5 g of purified water;

(5) 0.5 g of clidanac was added to 1.5 g of diisopropyl adipinate, and dissolved by warming at 50° C.; and (6) in a homomixer heated to 50° C., first solutions (2), (3) and (4) were added to mixture (1), and solution (5) was added, and the whole mixture was stirred, and cast in a mold. Thereafter, a soft patch was prepared in the same manner as Example 4.

In Examples 37–40, soft patches were prepared according to the formula of Table 1 in the same manner as Example 36.

EXAMPLES 41–47

Pindolol-containing preparations.

According to the formula of Table 1, soft patches were prepared in the same manner as Example 36.

Examples 48–51

Propranolol hydrochloride-containing preparations.

In Example 48, according to the formula given in Table 1, (1) 3 g of sodium citrate was dissolved in 20 g of purified water, and 20 g of gelatin was added to wet, and dissolved by warming at 50° C.;

(2) 10 g of casein sodium was dissolved in 10 g of purified water;

(3) 0.2 g of paraben was added to 20 g of glycerin, and dissolved by warming at 50° C., and 1 g of methyl cellulose was added to the solution;

(4) 1 g of Polysorbate 80 was dissolved in 5 g of purified water;

(5) 0.95 g of propranolol hydrochloride was dissolved in the remaining purified water;

(6) a mixture of 1 g of squalane and 3 g of octyldodecyl myristate was heated to 50° C.; and (7) in a homomixer heated to 50° C., first solutions (2), (3) and (4) were added to mixture (1), and solution (5) then solution (6) were added, and the whole mixture was stirred and cast into a mold. Thereafter, in the same manner as in Example 4, a soft patch was prepared.

In Examples 49–51, soft patches were prepared by the same procedure as Example 48 in accordance with the formula of Table 1.

Examples 52–56

Isosorbit nitrate-containing preparations.

In Example 52, according to the formula given in Table 1, (1) 30 g of purified water was added to wet 20 g of gelatin, which was dissolved by warming at 50° C.;

(2) 0.2 g of paraben was added to 10 g of glycerin, and was dissolved by warming at 50° C., then, after cooling, 2 g of karaya gum was added and suspended;

(3) 1 g of Polysorbate 80 was dissolved in 5 g of purified water;

(4) 1.25 g of isosorbit nitrate was suspended in sorbitol 5 g and remaining purified water;

(5) 4.5 g of squalane was heated to 50° C.; and (6) in a homomixer heated to 50° C., first solution (2) and (3) were added to mixture (1), and solution (4) was added then solution (5) was added, and the whole mixture was stirred and cast in a mold. Thereafter, in the same manner as in Example 4, a soft patch was prepared, In Examples 53–56, soft patches were prepared by the same procedure as Example 52 in accordance with the formula of Table 1.

Examples 57–59

N-methyl scopolamine methyl sulfate-containing preparations.

In Example 57, according to the formula given in Table 1, (1) 30 g of purified water was added to wet 20 g of gelatin, which was dissolved by warming at 50° C.;

(2) 10 g of purified water was added to 1 g of carrageenan to wet;

(3) 0.2 g of paraben was added to 20 g of glycerin, and dissolved by warming at 50° C.;

(4) 1 g of Polysorbate 80 was dissolved in 5 g of purified water;

(5) 0.095 g of N-methyl scopolamine methyl sulfate was added to the remaining purified water;

(6) a mixture of 3 g of silicone oil and 2 g of squalane was heated to 50° C.; and (7) in a homomixer heated to 50° C., first solutions (2), (3) and (4) were added to mixture (1), and solution (5) then solution (6) were added, and the whole mixture was stirred and cast into a mold. Thereafter, a soft patch was prepared in the same manner as Example 4.

In Examples 58–59, soft patches were prepared according to the formula of Table 1 in the same manner as Example 57.

Examples 60–61

Piroxicam-containing preparations.

According to the formula of Table 1, soft patches were prepared in the same manner as Example 4.

TABLE 1

(Note 1) (1)

| Material/Example | 1 | 2 | 3 | 4 | 5 | 6 | 7 | 8 | 9 | 10 | 11 | 12 |
|---|---|---|---|---|---|---|---|---|---|---|---|---|
| Drug | 1 | 1 | 0.5 | 1 | 1 | 1 | 1 | 1 | 1 | 1 | 1 | 1 |
| Gelatin | 15 | 12 | 20 | 20 | 20 | 20 | 20 | 15 | 15 | 25 | 22 | 22 |
| Casein sodium | | | | | | | | | | | | |
| Glycerin | 23 | 20 | 18 | 23 | 23 | 23 | 23 | 20 | 20 | 27 | 23 | 23 |
| Propylene glycol | | 5 | | | | | | | | | | |
| Sorbitol (70%) | | | 5 | | | | | | | | | |
| Butylene glycol | | | | | | | | | | | | |
| Polyethylene glycol | | | | | | | | | | | | |
| Pluran ® | 1 | | | 2 | 2 | 2 | 2 | 2 | 2 | 2 | 2 | 2 |
| Polyvinyl alcohol | 1 | | 2 | | | | 2 | | | | | |
| Methylcellulose | | | | | | | | | 1 | | | |
| Hydroxyethylcellulose | | 2 | | | | | | | | 1 | | |
| Sodium polyacrylate | 0.5 | 0.5 | 0.5 | 0.5 | 0.5 | 0.5 | 0.5 | 0.5 | 0.5 | 0.5 | 0.5 | 0.5 |
| Sodium alginate | | | | | | | | | | | | |
| Polyvinyl pyrrolidone | | | | | | | | | | | | |
| Hiviswako ® 105 | | | | | | | | | | | | |
| Karaya gum | | | | | | | | | | | | |
| Carrageenan | | | | | | | | | | | | |
| Squalane | | | | | | | | | | | | |
| Medium-chain fatty acid triglyceride (Note 2) | | | | 5 | 3 | 3 | 5 | 5 | 5 | | | 5 |
| Diisopropyl adipinate | 0.5 | 0.5 | 0.2 | | 1 | 1 | | | | | 5 | |
| Diethyl sebacate | | | | | | | | | | | | |
| White vaseline | | | | 3 | | | | 3 | 3 | 3 | | |
| Liquid paraffin | | | | | 5 | | | | | | | |
| Purified lanolin | | | | | | | | | | | 3 | 3 |
| Cetanol | | | | | | | 3 | | | | | |
| Stearyl alcohol | | | | | | | 3 | | | | | |
| Isopropyl myristate | | | | | | | | | | | | |
| Silicone oil | | | | | | | | | | 1 | | |
| Octyldodecyl myristate | | | | | | | | | | | | |
| Polysorbate 80 | 0.2 | 0.1 | | 1 | 1 | 1 | 1 | 1 | 1 | | 1 | 1 |
| Crotamiton | | | | | | | | | | | | |
| Sodium citrate | | | | 2 | 2 | 2 | | 2 | 2 | 3 | 3 | 3 |
| Other absorption promoting auxiliaries (Note 3) | | | | | | | | 2 | | | | |
| Paraben | 0.1 | 0.1 | 0.1 | 0.2 | 0.2 | 0.2 | 0.2 | 0.2 | 0.2 | 0.2 | 0.2 | 0.2 |
| Distilled water | 57.7 | 57.8 | 53.7 | 42.3 | 41.3 | 40.3 | 42.3 | 47.3 | 49.3 | 40.3 | 39.3 | 39.3 |

(Note 1) All amounts are by weight (g).
(Note 2) ODO ® (mixed caprylic-capric acid (75:25) triglyceride, manufactured by Nisshin Seiyu Kabushiki Kaisha in Japan)
(Note 3) Example 8: Azone ®; Example 25: urea; Example 26: allantoin; Example 27: salicylic acid; Example 42: Azone ®; Example 43: N—methyl-2-pyrrolidone; Example 44: 2-pyrrolidone; Example 45: N,N—dimethylacetamide.

TABLE 1

(Note 1) (2)

| Material/Example | 13 | 14 | 15 | 16 | 17 | 18 | 19 | 20 | 21 | 22 | 23 | 24 |
|---|---|---|---|---|---|---|---|---|---|---|---|---|
| Drug | 1 | 1 | 1 | 1 | 1 | 1 | 1 | 1 | 1 | 1 | 0.2 | 0.2 |
| Gelatin | 22 | 22 | 22 | 22 | 22 | 15 | 15 | 15 | 15 | 15 | 22 | 20 |
| Casein sodium | | | | | | | | | | 5 | | |
| Glycerin | 23 | 23 | 23 | 23 | 23 | 20 | 20 | 20 | 20 | 20 | 23 | 23 |
| Propylene glycol | | | | | | | | | | | | |
| Sorbitol (70%) | | | | | | | | | | | | |
| Butylene glycol | | | | | | | | | | | | |
| Polyethylene glycol | | | | | | | | | | | | |
| Pluran ® | 2 | 2 | 2 | 2 | 2 | 2 | | | | 2 | 2 | 2 |
| Polyvinyl alcohol | | | | | | | | | | | | |
| Methylcellulose | | | | | | | | | | | | |
| Hydroxyethylcellulose | | | | | | | | | | | | |
| Sodium polyacrylate | 0.5 | 0.5 | 0.5 | 0.5 | 0.5 | 0.5 | | 0.5 | | 0.5 | 0.5 | 0.5 |
| Sodium alginate | | | | | | | | | 1 | | | |
| Polyvinylpyrrolidone | | | | | | | | | | | | |
| Hiviswako ® 105 | | | | | | 1 | | | | | | |
| Karaya gum | | | | | | | 2 | | | | | |
| Carrageenan | | | | | | | | 1 | | | | |
| Squalane | | | | | | | | | | | | |
| Medium-chain fatty acid triglyceride (Note 2) | | 5 | 2.5 | 5 | 7.5 | 5 | 5 | 5 | 5 | 5 | 5 | 2.5 |
| Diisopropyl adipinate | | | | | | | | | | | | |
| Diethyl sebacate | | | | | | | | | | | | |
| White vaseline | 3 | 3 | 1.5 | | 4.5 | 3 | 3 | 3 | 3 | 3 | 3 | 1.5 |
| Liquid paraffin | | | | | | | | | | | | |
| Purified lanolin | | | | | | | | | | | | |
| Cetanol | | | | | | | | | | | | |
| Stearyl alcohol | | | | | | | | | | | | |
| Isobutyl myristate | 5 | | | | | | | | | | | |
| Silicone oil | | | | | | | | | | | | |
| Octyldodecyl myristate | | | | | | | | | | | | |

TABLE 1-continued

| Material/Example | 13 | 14 | 15 | 16 | 17 | 18 | 19 | 20 | 21 | 22 | 23 | 24 |
|---|---|---|---|---|---|---|---|---|---|---|---|---|
| | | | | (Note 1) (2) | | | | | | | | |
| Polysorbate 80 | 1 | 1 | 1 | 1 | 1 | 1 | 1 | 1 | 1 | 1 | 1 | 1 |
| Crotamiton | | | | | | | | | | | | |
| Sodium citrate | 3 | 3 | 3 | 3 | 3 | 2 | 2 | 2 | 2 | 2 | 3 | |
| Other absorption promoting auxiliaries (Note 3) | | | | | | | | | | | | |
| Paraben | 0.2 | 0.2 | 0.2 | 0.2 | 0.2 | 0.2 | 0.2 | 0.2 | 0.2 | 0.2 | 0.2 | 0.2 |
| Distilled water | 39.3 | 39.3 | 43.3 | 42.3 | 35.3 | 49.3 | 50.8 | 51.3 | 51.8 | 45.3 | 40.1 | 49.1 |

TABLE 1

| Material/Example | 25 | 26 | 27 | 28 | 29 | 30 | 31 | 32 | 33 | 34 | 35 | 36 |
|---|---|---|---|---|---|---|---|---|---|---|---|---|
| | | | | (Note 1) (3) | | | | | | | | |
| Drug | 0.2 | 0.2 | 0.2 | 1 | 1 | 1 | 1 | 1 | 0.4 | 0.4 | 0.4 | 0.5 |
| Galatin | 20 | 20 | 20 | 20 | 20 | 20 | 20 | 20 | 20 | 20 | 20 | 20 |
| Casein sodium | | | | | | | | | | | | |
| Glycerin | 23 | 23 | 23 | 20 | 20 | 20 | 20 | 20 | 17 | 17 | 17 | 23 |
| Propylene glycol | | | | | | | | | | | | |
| Sorbitol (70%) | | | | | | | | | | | | |
| Butylene glycol | | | | | | | | | | | | |
| Polyethylene glycol | | | | 7 | 7 | 7 | | | 3 | 3 | 3 | |
| Pluran ® | 2 | 2 | 2 | 2 | 2 | 2 | 2 | 2 | 2 | 2 | 2 | 2 |
| Polyvinyl alcohol | | | | | | | | | | | | |
| Methylcellulose | | | | | | | | | | | | |
| Hydroxyethylcellulose | | | | | | | | | | | | |
| Sodium polyacrylate | 0.5 | 0.5 | 0.5 | 0.5 | 0.5 | 0.5 | 0.5 | 0.5 | 0.5 | 0.5 | 0.5 | 0.5 |
| Sodium alginate | | | | | | | | | | | | |
| Polyvinylpryrrolidone | | | | | | | | | 3 | | | |
| Hiviswako ® 105 | | | | | | | | | | | | |
| Karaya gum | | | | | | | | | | | | |
| Carrageenan | | | | | | | | | | | | |
| Squalane | | | | | | | | | | | | |
| Medium-chain fatty acid triglyceride (Note 2) | 2.5 | 2.5 | 2.5 | 2 | | 3 | | | 1.5 | | | |
| Diisopropylagipinate | | | | | | | | | | | | 1.5 |
| Diethy sebacate | | | | | 3 | | 5 | 5 | | | 1.5 | |
| White vaseline | 1.5 | 1.5 | 1.5 | | | | | | | | | |
| Liquid paraffin | | | | | | | 2 | | | | | |
| Purified lanolin | | | | 1 | | | | | | | | |
| Cetanol | | | | | | | | | | | | |
| Stearyl alcohol | | | | | | | | | | | | |
| Isopropyl myristate | | | | | | | | | | 1.5 | | |
| Silicone oil | | | | | | | | | | | | |
| Octyldodecyl myristate | | | | | | | | | | | | |
| Polysorbate 80 | 1 | 1 | 1 | 1 | 1 | 1 | 1 | 1 | 1 | 1 | 1 | 1 |
| Crotamiton | | | | | | | 2 | | | | | |
| Sodium citrate | | | | | | | | | 2 | 2 | 2 | |
| Other absorption promoting auxiliaries (Note 3) | 2 | 2 | 0.2 | | | | | | | | | |
| Paraben | 0.2 | 0.2 | | 0.2 | 0.2 | 0.2 | 0.2 | 0.2 | 0.2 | 0.2 | 0.2 | 0.2 |
| Distilled water | 47.1 | 47.1 | 49.1 | 45.3 | 45.3 | 41.3 | 50.3 | 47.3 | 52.4 | 52.4 | 52.4 | 51.3 |

TABLE 1

| Material/Example | 37 | 38 | 39 | 40 | 41 | 42 | 43 | 44 | 45 | 46 | 47 | 48 |
|---|---|---|---|---|---|---|---|---|---|---|---|---|
| | | | | (Note 1) (4) | | | | | | | | |
| Drug | 0.5 | 0.5 | 0.5 | 1 | 1 | 1 | 1 | 1 | 1 | 1 | 1 | 0.95 |
| Gelatin | 20 | 20 | 20 | 20 | 20 | 20 | 20 | 20 | 20 | 20 | 20 | 20 |
| Casein sodium | | | | | | | | | | | | 10 |
| Glycein | 23 | 23 | 20 | 20 | 20 | 20 | 20 | 20 | 20 | 20 | 17 | 20 |
| Propylene glycol | | | | | | | | | | | | |
| Sorbitol (70%) | | | | | | | | | | | | |
| Butylene glycol | | | 2 | | | | | | | | 2 | |
| Polyethylene glycol | | | | | | | | | | | | |
| Pluran ® | 2 | 2 | 2 | 2 | 2 | 2 | 2 | 2 | 2 | 2 | 2 | 2 |
| Polyvinyl alcohol | | | | | | | | | | | | |
| Methylcellulose | | | | | | | | | | | | |
| Hydroxyethylcellulose | | | | | | | | | | | | |
| Sodium polyacrylate | 0.5 | 0.5 | 0.5 | | 0.5 | 0.5 | 0.5 | 0.5 | 0.5 | 0.5 | 0.5 | |
| Sodium alginate | | | | | | | | | | | | |
| Polyvinylpyrrolidone | | | | | | | | | | | | |
| Hiviswako ® 105 | | | | | | | | | | | | |
| Karaya gum | | | | | | | | | | | | |
| Carrageenan | | | | | | | | | | | | |
| Squalane | | | | | | | | | | | | 1 |
| Medium-chain fatty acid triglyceride (Note 2) | | | | | | | | 3 | 1.5 | | | |

TABLE 1-continued (Note 1) (4)

| Material/Example | 37 | 38 | 39 | 40 | 41 | 42 | 43 | 44 | 45 | 46 | 47 | 48 |
|---|---|---|---|---|---|---|---|---|---|---|---|---|
| Diisopropyl adipinate | | | 1.5 | 2.5 | 1.5 | | | | 0.5 | | | |
| Diethyl sebacate | 1.5 | | | | | 1.5 | 1.5 | | | | | |
| White vaseline | | | | | | | | | | | | |
| Liquid paraffin | | | | | | | | 2 | | | | |
| Purified lanolin | | | | | | | | | | | | |
| Cetanol | | | | | | | | | | | | |
| Stearyl alcohol | | | | | | | | | | | | |
| Isopropyl myristate | | 2 | | | | | 1 | | | | | |
| Silicone oil | | | | | | | | | | | | |
| Octyldodecyl myristate | | | | | | | | | | 5 | 3 | 3 |
| Polysorbate 80 | 1 | 1 | 1 | 1 | 1 | 1 | 1 | 1 | 1 | 1 | 1 | 1 |
| Crotamiton | | | | | | | | | | | | |
| Sodium citrate | | | | | | | | | | | | 3 |
| Other absorption promoting auxiliaries (Note 3) | | | | | | 1 | 1 | 1 | 1 | | | |
| Paraben | 0.2 | 0.2 | 0.2 | | 0.5 | 0.5 | 0.5 | 0.5 | 0.5 | 0.5 | 0.5 | 0.2 |
| Distilled water | 51.3 | 50.8 | 52.3 | 53.5 | 53.5 | 52.5 | 51.5 | 49.0 | 52.0 | 50.0 | 53.0 | 42.6 |

TABLE 1

(Note 1) (5)

| Material/Example | 49 | 50 | 51 | 52 | 53 | 54 | 55 | 56 | 57 | 58 | 59 | 60 | 61 |
|---|---|---|---|---|---|---|---|---|---|---|---|---|---|
| Drug | 0.95 | 0.95 | 0.95 | 1.25 | 1.25 | 1.25 | 1.25 | 1.25 | 0.095 | 0.095 | 0.095 | 0.12 | 0.02 |
| Gelatin | 20 | 15 | 10 | 20 | 17 | 20 | 17 | 20 | 20 | 15 | 20 | 20 | 20 |
| Casein sodium | | | | | | | | | | 10 | 5 | | |
| Glycerin | | | 10 | 10 | 10 | 17 | 5 | 20 | 20 | | 13 | 23 | 25 |
| Propylene glycol | | 2 | | | 3 | | | | | 1 | | | |
| Sorbitol (70%) | 10 | 10 | 5 | 5 | | | 10 | | | 7 | 7 | | |
| Butylene glycol | 3 | | | | | | | | | 3 | | | |
| Polyethylene glycol | | | | 5 | | | | | | | | | |
| Pluran ® | | | | | | | | | | | | | 2 |
| Polyvinyl alcohol | | | | 2 | 2 | 2 | 2 | | | | | | |
| Methylcellulose | | | 1 | | | | | | | 1 | | | |
| Hydroxyethylcellulose | | | | 2 | | 2 | | | | | | | |
| Sodium polyacrylate | | 0.4 | | | 0.5 | 0.5 | 0.5 | | | 0.5 | 0.5 | 0.5 | 0.5 |
| Sodium alginate | | | | | | | | | | | | | |
| Polyvinyl pyrrolidone | | | | | | | 2 | 2 | | | | | |
| Hiviswako ® 105 | | | 0.3 | | | | | | | | | | |
| Karaya gum | 2 | | | 2 | 2 | 1 | | | | 1 | 1.5 | | |
| Carrageenan | | | | | | | | | 1 | 1 | | | |
| Squalane | | | | 4.5 | | | | | 2 | | | | |
| Medium-chain fatty acid triglyceride (Note 2) | | | | | | | 3 | 3 | | 3 | | 0.5 | |
| Diisopropyl adipinate | | 1.5 | 1 | | 2 | | | | | | | | |
| Diethyl sebacate | 3 | | | | | | | | | | 2 | | 1 |
| White vaseline | | | | | | | | | | 1.5 | 1 | | |
| Liquid paraffin | | | | | 1 | | | | | | | | 1 |
| Purified lanolin | 1 | 1 | 0.5 | | 2.5 | | 2.5 | 4.5 | | | | | |
| Cetanol | | 3 | | | | | | | | | | | |
| Stearyl alcohol | | 3 | | | | | | | | | | | |
| Isopropyl myristate | | | | | | | | | | | | | |
| Silicone oil | | | | | 1 | 5 | | 3 | | | | | |
| Octyldodecyl myristate | | | | 3 | | | | | | | | | |
| Polysorbate 80 | 1 | 1 | 1 | 1 | 1 | 1 | 1.5 | 1.5 | 1 | 1 | 1 | 0.2 | 0.5 |
| Crotamiton | | | | | | | | | | | | | |
| Sodium citrate | 3 | 3 | 3 | | | | | | | | | | |
| Other absorption promoting auxiliaries (Note 3) | | | | | | | | | | | | | |
| Paraben | 0.2 | 0.2 | 0.2 | 0.2 | 0.2 | 0.2 | 0.2 | 0.2 | 0.2 | 0.2 | 0.2 | 0.2 | 0.2 |
| Distilled water | 57.69 | 61.19 | 68.49 | 58.52 | 56.52 | 52.52 | 50.52 | 47.532 | 52.889 | 54.889 | 48.889 | 55.48 | 49.78 |

The external preparation obtainable by the above method of this invention can be stored in stable condition, and when applied, ensures adequate tackiness and adhesivity to the human skin and mucosa with a good feeling of use. Left on the skin for a long time, it does not cause side effects such as contact dermatitis, and can be easily detached after use. Thus, having the characteristics summarized below, the preparation according to this invention has great clinical and industrial values.

(a) Compared with the conventional external drugs such as ointments, the preparation of this invention is convenient in use and permits easy control of dosage. Therefore, one may avoid occurrence of side effects and losses of the drug due to overdosing or inadequate efficacies due to underdosing, thus instituting a pinpointed regimen for each therapeutic purpose and each disease.

(b) The preparation ensures a high percutaneous absorption of the active component drug. Therefore, not only local effects but also the systemic effects can be expected, (c) Being a soft preparation, the preparation is flexible and offers good contact with the skin and a satisfactory feeling of use.

(d) The drugs which would cause side effects, e.g. gastrointestinal disorders, or poor bioavailability can be effectively used in an improved manner, e.g. delayed metabolism.

(e) When the treatment regimen calls for several oral intakes a day, the patient may forget or dislike the taking of the drug. There also are cases in which many different drugs must be taken in large amounts. In such cases, the soft patch according to this invention ensures many hours of sustained efficacy at the application interval of once or twice daily. Thus, it is easy for the patient to use and for the doctor to control both the disease and drug effect.

The test examples of this invention are given below.

TEST EXAMPLE 1

Sensory test on feeling of use such as fitness, adhesion, etc.

Using the soft patch of the formula of Example 4 from which the drug had been removed, a sensory test was performed in duplicate using a panel of 10 adults in accordance with Scheffe's method described in Handbook of Sensory Tests, New Edition, pages 356–366 (The Japanese Federation of Science and Technology). Thus, test samples were applied to the right and left upper arms and, after 2 hours, removed. The panelists were asked to evaluate the feeling of use for each of the right and left arms and to score it on the following scale: much better (+3), certainly better (+2), somewhat better (+1), no different (0), somewhat worse (−1), worse (−2) and much worse (−3).

The ultimate mean score about the feeling of use of the above soft patch was +2.04±0.78. The concurrent test with the commercial control plaster gave the score of −0.73±0.83. Aside from the above result, the panelists pointed out that the feeling of the soft patch to the skin was superior to the conventional external drugs.

TEST EXAMPLE 2

Concentration in serum after administration of ifenprodil tartrate-containing preparation.

Method

The hairs on the back of male albino rabbits (weighing 3.1 to 4.3 kg, groups of 3 rabbits) were clipped off with electric clippers with care not to injure the skin on the day before administration of test materials, and the following external preparations (C) to (I) of this invention were applied to the clipped area. Separately, by way of comparison, external preparation (B) and oral preparation (A) not containing oleaginous substance were prepared and applied. For both external and oral routes, the dosage was equally 10 mg/kg of ifenprodil tartrate.

(A) Aqueous solution containing 0.15% of ifenprodil tartrate.

(B) This external preparation was made as follows:

(1) 20 g of gelatin was wetted in 30 g of purified water, and dissolved by warming at 50° C.;

(2) 5 g of Pluran was dissolved in 10 g of purified water;

(3) 23 g of glycerin, 0.2 g of paraben, and 1 g of ifenprodil tartrate were added to 10.8 g of purified water, and blended well by warming at 50° C.; and (4) in a homomixer heated to 50° C., first solution (2) was added to solution (1), then solution (3) was added, and the whole mixture was stirred, and cast into a mold. After cooling, the molding was cut to make a thin film soft patch measuring 6.5 cm in length by 6.5 cm in width by 0.4 mm in thickness.

(C) A soft patch according to Example 10.
(D) A soft patch according to Example 11.
(E) A soft patch according to Example 12.
(F) A soft patch according to Example 13.
(G) A soft patch according to Example 14.
(H) A soft patch according to Example 15.
(I) A soft patch according to Example 16.

Blood samples of 3.5 to 4 ml aliquots were taken at timed intervals in 0.25 to 8 hours after administration in groups (A) and (B), and in 2 to 30 hours in groups (C) to (I), and the serum was separated by centrifugation. A 2 ml portion of the serum was extracted with ether and the extract was reacted with pentafluorobenzyl bromide in the presence of a strong alkali, and then with bis(trimethylsilyl)trifluoroacetamide. The resulting derivative was assayed by ECD-gas chromatography ($^{63}$Ni, model GLC-4CM of Shimadzu Corporation).

Results

The results are set forthe in Table 2, which discloses the following findings:

(1) The AUC (area under concentration in serum of the soft patch (B) was about half that of oral preparation (A).

(2) In the soft patches (C) to (I) which have oleaginous substances added to this soft patch (B), higher concentrations in the blood, longer persistance thereof, and higher AUC values were commonly noted as compared with those of (A) and (B) above. In particular, the soft patch (G) showed a Cmax (the maximum concentration in serum) of about 4 times higher, and the AUC value of about 24 times higher than (A).

TABLE 2

Concentration in Serum of Ifenprodil (Unchanged Form) (μg/ml)

| Group | Time (hr) 0.25 | 0.5 | 1 | 2 | 4 | 6 | 8 | AUC (ng·hr·ml$^{-1}$) |
|---|---|---|---|---|---|---|---|---|
| (A) | 1.0 ± 1.0 | 1.9 ± 1.0 | 5.0 ± 0.2 | 3.4 ± 0.4 | 3.2 ± 0.6 | 0 | — | 16.3 ± 1.1 |
| (B) | — | — | 1.9 ± 0.7 | 2.5 ± 1.0 | 0.8 ± 0.3 | 0.8 ± 0.2 | 0.5 ± 0.3 | 8.9 ± 1.7 |

| Group | Time (hr) 2 | 4 | 8 | 24 | 28 | 30 | AUC (ng·hr·ml$^{-1}$) |
|---|---|---|---|---|---|---|---|
| (C) | 0.4 ± 0.3 | 0.6 ± 0.2 | 1.1 ± 0.4 | 4.8 ± 2.7 | — | — | 51.8 ± 25.3 |
| (D) | 1.5 ± 0.2 | 1.7 ± 0.4 | 4.2 ± 0.3 | 3.2 ± 0.4 | 2.5 ± 0.2 | 2.4 ± 0.1 | 92.4 ± 8.3 |
| (E) | 1.9 ± 0.3 | 3.1 ± 0.8 | 7.3 ± 2.5 | 18.0 ± 4.4 | 4.9 ± 0.5 | 3.3 ± 0.3 | 286.0 ± 71.1 |
| (F) | 1.0 ± 0.9 | 4.4 ± 2.6 | 6.4 ± 2.8 | 12.2 ± 2.5 | 3.3 ± 0.9 | 3.5 ± 1.3 | 215.1 ± 59.7 |
| (G) | 0.6 ± 0.2 | 4.6 ± 1.5 | 15.5 ± 4.3 | 19.3 ± 0.8 | 9.0 ± 1.6 | 5.7 ± 0.5 | 395.5 ± 41.6 |
| (H) | 2.3 ± 1.2 | 3.7 ± 1.8 | 6.0 ± 3.0 | 9.6 ± 3.2 | 4.0 ± 0.8 | 4.0 ± 0.9 | 188.0 ± 62.7 |
| (I) | 1.1 ± 0.2 | 1.1 ± 0.1 | 4.7 ± 1.9 | 14.1 ± 2.3 | 4.8 ± 0.6 | 3.1 ± 0.4 | 209.8 ± 38.9 |

TEST EXAMPLE 3

Concentration in serum after administration of piroxicam-containing preparation.

Method

Part of dorsal hair of male SD rats (weighing 250 to 290 g, groups of 3 rats) was clipped off, and the following test materials (A) and (B) were attached or applied to the clipped area (3 cm by 3 cm=9 cm$^2$). The dosage was 0.5 mg/kg of piroxicam.

(A) A soft patch according to Example 60.

(B) A known preparation: An ointment containing piroxicam as disclosed in the Japanese Kokai Sho. No. 59-13714 comprising 0.5 g of piroxicam, 1.0 g of Hiviswako ® 105, 1.3 g of diisopropyanolamine, 2 g of glycerin, 5 g of 1,3-butyleneglycol, 30 g of ethanol, and 60.2 g of purified water.

After application of the test materials (A) and (B), the concentration of piroxicam in the serum was determined by the fluorometric method (measuring wavelength of 370 nm) according to a procedure proposed in a paper [Shichikawa et al., Rheumatism, No. 20, p. 214 (1980), published by the Japan Society of Rheumatism].

Results

Results are shown in Table 3.

TABLE 3

| | Centration in Serum of Piroxicam (μ/ml) | | | |
|---|---|---|---|---|
| | Time (hr) | | | AUC |
| Group | 1 | 3 | 6 | (μg · hr · ml$^{-1}$) |
| Soft patch according to Example 60 | 0.23 | 0.51 | 0.79 | 2.81 |
| Known preparation | 0.02 | 0.29 | 0.18 | 1.03 |

It thus disclosed that the preparation of this invention presents an AUC value about 2.7 times higher than a known preparation, and contributed to an increase of the percutaneous absorption of the drug.

We claim:

1. In the art of externally applying drug preparations to the skin, which act as a barrier to the absorption of the drug, the improvement which comprises externally contacting the skin with a soft drug preparation containing a percutaneously absorbable drug, applied either topically, directly to the effected site, or in the neighborhood thereof, for the purpose of curing disease on the skin surface, or under the skin, or to systematically reach a target tissue or organ, when absorbed from the skin surface where applied, at a site which is most conductive to the percutaneous absorption of the active components of the drug preparation and where a horny layer is not well developed, said drug preparation exhibiting a stick-itself-to-the-skin property and containing the following components:

(a) a percutaneously absorbable drug;

(b) a water-soluble protein having an absorption promoting effect in an amount which ranges from 5 to 15 weight percent based on the weight of the whole composition;

(c) a polyhydric alcohol in an amount which ranges from 5 to 50 weight percent based on the weight of the whole composition;

(d) a tackifier in an amount which ranges from 0.1 to 15 weight percent based on the weight of the whole composition; and (e) an oleaginous substance in an amount which ranges from 0.1 to 25 weight percent based on the weight of the whole composition.

2. The improvement according to claim 1, wherein an amount of the oleaginous substance ranges from 0.5 to 15 weight percent, based on the weight of the whole composition.

3. The improvement according to claim 1, wherein an amount of the drug ranges from 0.01 to 15 weight percent, based on the weight of the whole composition.

4. The improvement according to claim 1, wherein an amount of the water-soluble protein having an absorption promoting effect ranges from 10 to 30 weight percent, based on the weight of the whole composition.

5. The improvement according to claim 1, wherein an amount of polyhydric alcohol ranges from 10 to 30 weight percent, based on the weight of the whole composition.

6. The improvement according to claim 1, wherein an amount of the tackifier ranges from 0.5 to 10 weight percent, based on the weight of the whole composition.

7. The according to claim 1, wherein water is contained in addition to the components (a), (b), (c), (d) and (e).

8. The improvement according to claim 1, wherein the oleaginous substance is at least one member selected from the group consisting of esters of fatty acids, aliphatic higher alcohols, paraffin oils, lanolin oil and silicone oil.

9. The improvement according to claim 3, wherein the drug is one which exerts actions on circulatory system, nervous system, endocrine system, respiratory system, metabolic system, urinary organ system or digestive organ system.

10. The improvement according to claim 1, wherein the water-soluble protein is at least one member selected from the group consisting of animal proteins, vegetable proteins and peptides.

11. The improvement according to claim 1, wherein the polyhydric alcohol has 2 to 6 of alcoholic hydroxyl groups.

12. The improvement according to claim 1, wherein the tackifier is at least one member selected from the group consisting of cellulose derivatives, polysaccharides, carboxyvinyl polymers, polyvinyl alcohol and polyvinylpyrrolidone.

13. The improvement according to claim 7, wherein adsorption promoting auxiliaries, preservatives, emulsified-dispersants, pH-controlling agent or colors are additionally admixed.

14. The improvement according to claim 1, wherein the oleaginous substance is at least one member selected the group consisting of esters of medium to higher fatty acids containing 6–20 carbon atoms and aliphatic monools or triols containing 1–20 carbon atoms, or polyols containing 4–8 hydroxyl groups; aliphatic higher alcohols containing 14–20 carbon atoms; fluid paraffin; white vaseline; lanolin; and silicone.

15. The improvement according to claim 1, wherein the oleaginous substance is triglycerides of medium to higher fatty acids containing 6–20 carbon atoms or esters of said fatty acids and aliphatic monools containing 1–20 carbon atoms.

* * * * *